US012083218B2

(12) United States Patent
Koll et al.

(10) Patent No.: US 12,083,218 B2
(45) Date of Patent: Sep. 10, 2024

(54) SOFT CHEWABLE DOSAGE FORM

(71) Applicant: Johnson & Johnson Consumer Inc., Skillman, NJ (US)

(72) Inventors: Gregory E. Koll, Hillsborough, NJ (US); Gerard P. McNally, Derwyn, PA (US); Vipul Dave, Hillsborough, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 443 days.

(21) Appl. No.: 17/447,453

(22) Filed: Sep. 13, 2021

(65) Prior Publication Data

US 2021/0401739 A1 Dec. 30, 2021

Related U.S. Application Data

(62) Division of application No. 16/654,107, filed on Oct. 16, 2019, now Pat. No. 11,141,375.

(60) Provisional application No. 62/747,267, filed on Oct. 18, 2018.

(51) Int. Cl.

| | |
|---|---|
| ***A61K 9/00*** | (2006.01) |
| ***A23L 27/00*** | (2016.01) |
| ***A23L 27/30*** | (2016.01) |
| ***A23L 33/10*** | (2016.01) |
| ***A61K 9/127*** | (2006.01) |
| ***A61K 31/426*** | (2006.01) |

(52) U.S. Cl.
CPC ............ *A61K 9/0056* (2013.01); *A23L 27/33* (2016.08); *A23L 27/84* (2016.08); *A23L 33/10* (2016.08); *A61K 9/127* (2013.01); *A61K 31/426* (2013.01)

(58) Field of Classification Search
CPC ............................ A61K 9/0056; A61K 31/456
See application file for complete search history.

(56) References Cited

U.S. PATENT DOCUMENTS

| | | | |
|---|---|---|---|
| 4,597,981 | A | 7/1986 | Kastin |
| 4,684,534 | A | 8/1987 | Valentine |
| 5,817,340 | A | 10/1998 | Roche et al. |
| 8,865,240 | B2 | 10/2014 | Paulsen et al. |
| 9,381,155 | B2 | 7/2016 | Paulsen et al. |
| 2007/0269577 | A1 | 11/2007 | Pershad et al. |
| 2013/0052252 | A1 | 2/2013 | Bell et al. |

(Continued)

FOREIGN PATENT DOCUMENTS

| | | | |
|---|---|---|---|
| EP | 2085079 | A | 8/2009 |
| EP | 2709641 | A | 3/2014 |
| EP | 3188718 | A | 7/2017 |

(Continued)

OTHER PUBLICATIONS

International search report and written opinion dated Jan. 23, 2020, for international application PCT/IB2019/058820.

*Primary Examiner* — Carlos A Azpuru

(57) ABSTRACT

The invention relates to a soft chewable dosage form comprising a first active pharmaceutical ingredient encapsulated in a lipid material that is embedded in the soft chewable dosage form and wherein the soft chewable dosage form comprises at least a second active pharmaceutical ingredient as well as a method of treating a subject suffering from a disease or disorder in the gastro intestinal tract using the soft chewable dosage form.

3 Claims, 1 Drawing Sheet

(56) References Cited

U.S. PATENT DOCUMENTS

| | | | |
|---|---|---|---|
| 2014/0242214 | A1 | 8/2014 | Boghani et al. |
| 2018/0169008 | A1 | 6/2018 | Dixit et al. |

FOREIGN PATENT DOCUMENTS

| | | | | |
|---|---|---|---|---|
| WO | 94/12180 | | * | 6/1994 |
| WO | WO 1994/012180 | A | | 6/1994 |
| WO | WO 1998/020860 | A | | 5/1998 |
| WO | WO 2000/016743 | A | | 3/2000 |
| WO | WO 2003/088755 | A | | 10/2003 |
| WO | WO 2008/094877 | A | | 8/2008 |
| WO | 2017091166 | A1 | * | 6/2017 |
| WO | WO 2017/091166 | A | | 6/2017 |

* cited by examiner

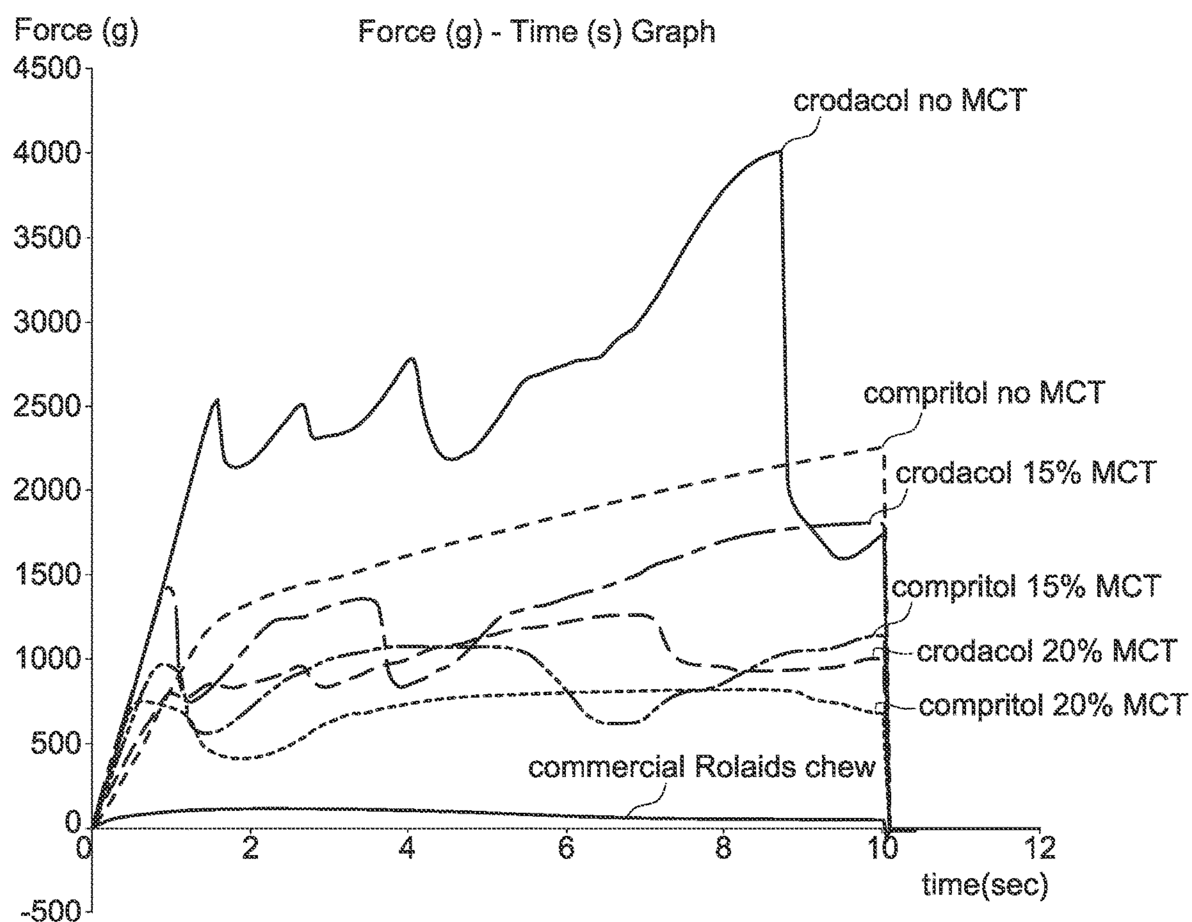
Force (g)
Force (g) - Time (s) Graph
4500
4000
3500
3000
2500
2000
1500
1000
500
0
-500
0
2
4
6
8
10
12
time(sec)
crodacol no MCT
compritol no MCT
crodacol 15% MCT
compritol 15% MCT
crodacol 20% MCT
compritol 20% MCT
commercial Rolaids chew

SOFT CHEWABLE DOSAGE FORM

CROSS-REFERENCE TO RELATED APPLICATION

This application is a divisional of U.S. application Ser. No. 16/654,107 filed Oct. 16, 2019, which claims the benefit of U.S. application 62/747,267 filed on Oct. 18, 2018, the complete disclosure of which is hereby incorporated herein by reference for all purposes.

FIELD OF INVENTION

The invention relates to a soft chewable dosage form comprising a first active pharmaceutical ingredient encapsulated in a lipid material/matrix that is embedded in a soft chewable dosage form and wherein the soft chewable dosage form comprises at least a second active pharmaceutical ingredient, as well as a method of treating a subject suffering from a disease or disorder in the gastro intestinal tract using such a soft chewable dosage form.

BACKGROUND OF INVENTION

Histamine H2-receptor antagonists, for example cimetidine, ranitidine, nizetidine, roxatine and famotidine, reduce acid secretion by acting directly on the acid-secreting parietal cell located within the gastric gland of the stomach wall.

Although histamine H2-receptor antagonists are remarkably effective in the treatment of many gastric disorders, in particular peptic and gastric ulcers, there exist certain patient groups which do not respond to treatment. In addition, the time lapse between dosing and onset of action limits the potential benefit of histamine H2-receptor antagonists in the treatment of acute, self-limiting gastric disorders.

Histamine H2-receptor antagonists are of potential benefit in the self-medication of acute, self-limiting gastric disorders such as hyperacidity. However, their slow onset of action is unlikely to meet the consumer requirement for rapid relief of symptoms.

Co-administration of histamine H2-receptor antagonists and other pharmaceutically active materials, including antacids, has been investigated. The rationale for co-administration with antacid is that the antacid brings about rapid relief from the symptoms of excess stomach acidity by neutralization whereas the histamine H2-receptor antagonist acts independently by inhibiting secretion of acid from the parietal cell.

Antacids used today are made from a variety of inorganic salts such as calcium carbonate, sodium bicarbonate, magnesium salts and aluminum salts. Magnesium hydroxide and aluminum hydroxide are the most potent magnesium and aluminum salts and are often used in combination. In addition, aluminum oxide, magnesium oxide, magnesium carbonate, aluminum phosphate, magaldrate, magnesium trisilicate, and aluminum sucrose sulfate (sucralfate) are also employed.

However, co-administration of famotidine is often very difficult because famotidine is extremely sensitive to humidity and can immediately start to degrade in such conditions.

SUMMARY OF THE INVENTION

The invention relates to the development of new improved soft chewable dosage form comprising a first active pharmaceutical ingredient encapsulated in a lipid material/matrix that is embedded in a soft chewable dosage form and wherein the soft chewable dosage form comprises at least a second active pharmaceutical ingredient. One example comprises famotidine encapsulated in a lipid material and embedded in a soft chewable dosage form comprising at least one antacid.

The invention enables for the first time the delivery of a famotidine/antacid combination in a soft chewable dosage form. The format ensures the stability of famotidine and offers a better sensory experience in terms of soothing and coating the painful esophageal tissues, giving consumers a faster acting remedy.

Soft chew forms inherently have a high-water content. A high level of water can contribute to degradation (hydrolysis of famotidine) if raw famotidine is blended into the matrix. In the case of the present invention, the lipid insert/material prevents ingress of water into the famotidine particles and prevents further interaction and hydrolysis.

Finally, the invention relates to a method of using the soft chewable tablet as defined above and below in the application for the treatment of a subject suffering from a disease or disorder in the gastro intestinal tract, such as heart burn.

BRIEF DESCRIPTION OF THE DRAWING

FIG. 1 shows force measurements on samples with different amounts of MCTs.

DETAILED DESCRIPTION OF EMBODIMENTS OF THE INVENTION

Definitions

In the context of the present application and invention the following definitions apply:

The term "soft chewable" is intended to mean a dosage form which retains its integrity and texture upon chewing, does not break into discrete, solid pieces or particulates upon chewing and is intended to be swallowed. The soft chew is palatable, edible, and is similar in texture to confectionery taffy or nougat.

The term "% w/w" is intended to mean the percentage of an ingredient(s)/the total percentage by weight of the composition (100%).

A "dosage", "dosage form", "dose unit" or "dose" as used herein means the amount of a pharmaceutical ingredient comprising therapeutically active agent(s) administered at a time. "Dosage", "dosage form", "dose unit" or "dose" includes administration of one or more units of pharmaceutical ingredient administered at the same time.

The term "gastric disease or disorder" is primarily intended to mean an increased production of the acid secretion which leads to heartburn and bothersome gas symptoms in a subject, also named indigestion. Indigestion, also known as dyspepsia, is a condition of impaired digestion. Symptoms may include upper abdominal fullness, heartburn, nausea, belching, or upper abdominal pain. People may also experience feeling full earlier than expected when eating. Dyspepsia is a common problem and is frequently caused by gastroesophageal reflux disease (GERD) or gastritis.

The Soft Chewable Dosage Form

In one embodiment the invention relates to a soft chewable dosage form comprising a first active pharmaceutical ingredient encapsulated in a lipid material/matrix that is embedded in a soft chewable dosage form and wherein the soft chewable dosage form comprises at least a second active pharmaceutical ingredient.

In one example the encapsulated active pharmaceutical ingredient comprises at least one histamine H2-receptor antagonist, such as cimetidine, ranitidine, nizatidine, roxatidine and famotidine, their pharmaceutically acceptable salts, isomers and salts of isomers.

In another embodiment the H2 receptor antagonist is famotidine and the second active pharmaceutical ingredient is at least one antacid.

The particle size of the lipid encapsulated famotidine is from about 100 microns to about 5000 microns, such as from about 200 microns to about 2000 microns.

The famotidine is embedded and present in the dosage form within a lipid matrix as a solid bead. The bead may be applied on the surface or inserted (as an insert) into the soft chew dosage form. In order to prepare this bead, famotidine is suspended or dispersed in a lipid base and deposited as a bead. It may be deposited and solidified as a bead which is later applied to the soft chew; or applied in a liquid form and deposited on the soft chew which is solidified in-situ. This solidification may be facilitated by an additional cooling step at room temperature, or a temperature cooler that room temperature (25° C.). The famotidine is present in the lipid bead as a dispersed solid or in a solid solution.

The diameter of the lipid bead of the present invention is from about 2 millimeters to about 15, or from about 3 millimeters to about 8 millimeters. The weight of the lipid bead can range from about 20 mg to about 150 mg, or from about 30 mg to about 80 mg.

In another embodiment, the famotidine is present as a plurality of particulates, wherein such particulates are coated with at least one lipid material or polymer. As used herein, a plurality of particulates is defined of at least two particulate units comprising famotidine.

The at least one antacid is selected from the group consisting of calcium carbonate, sodium bicarbonate, magnesium hydroxide, aluminum oxide, aluminum hydroxide, magnesium oxide, magnesium carbonate, aluminum phosphate, magaldrate and magnesium trisilicate.

The lipid material that encapsulates/coats the active pharmaceutical ingredient is selected from the group consisting of Cetostearyl alcohol, Glyceryl dibehenate, glyceryl palmitostearate, mono/diglycerides or hydrogenated vegetable oil or vegetable oil. Other examples of lipid materials include, but are not limited to, fatty acid esters such as sucrose fatty acid esters, mono, di, and triglycerides, glyceryl monostearate, glyceryl tristearate, glyceryl trilaurylate, glyceryl myristate, GlycoWax-932, lauroyl macrogol-32 glycerides, and stearoyl macrogol-32 glycerides; phospholipids such as phospholipids include phosphotidyl choline, phosphotidyl serene, phosphotidyl enositol, and phosphotidic acid; waxes such as carnauba wax, spermaceti wax, beeswax, candelilla wax, shellac wax, microcrystalline wax, and paraffin wax; and fats such as hydrogenated vegetable oils such as for example cocoa butter, hydrogenated palm kernel oil, hydrogenated cottonseed oil, hydrogenated sunflower oil, and hydrogenated soybean oil; and free fatty acids and their salts. These lipids are also suitable for use as the primary lipid within the lipid bead or material.

In certain embodiments an emulsifier or a second lipid may be added to the primary lipid in order to soften or modify the texture of the lipid bead or material. The second lipid may also act as a plasticizer. Emulsifiers include but are not limited to polyethylene sorbitan monooleate (polysorbate 60 and 80), glycerides, glyceryl esters, glyceryl monolineoleate, and monolineoleate. Suitable second lipids for use as a plasticizer include but are not limited to medium chain triglycerides (MCTs). The emulsifier or second lipid (plasticizer) may be present within the lipid bead or material at an amount from about 5 percent to about 50 percent, or from about 5 percent to about 30 percent by weight of the lipid bead or material.

If famotidine is the active pharmaceutical ingredient it may be in the form of granulate, bead or compressed tablet.

In addition to famotidine and antacid(s) the soft chewable dosage form may also comprise simethicone as an active pharmaceutical ingredient. Simethicone may be present in the soft chew base comprising antacid, or in the lipid bead or pellet comprising famotidine.

The soft chewable tablet may further comprise one or more ingredient(s) selected from the list consisting of fats, proteins, colorings, flavors, sweeteners, thickeners, emulsifiers, antioxidants, preservatives, lubricants, glidants, gelling agents and disintegrants.

Example of flavors are peppermint, spearmint, eucalyptus, licorice, vanilla, caramel, mixed berries, mixed fruits, black current, blue berry, cherry and lemon.

If needed one or more of the active pharmaceutical ingredients are taste masked. Taste masking technologies are well known for a person skilled in the art.

Examples of excipients include fats, proteins, fillers, glidants, lubricants, sweeteners, flavors, coloring agents, fillers, binding/gelling agents and mixtures thereof.

Suitable lubricants include long chain fatty acids and their salts, such as magnesium stearate and stearic acid, talc, glycerides waxes, and mixtures thereof.

Suitable glidants include colloidal silicon dioxide.

Examples of sweeteners include, synthetic or natural sugars; artificial sweeteners such as saccharin, sodium saccharin, sucralose, aspartame, acesulfame, thaumatin, glycyrrhizin, sucralose, cyclamate, dihydrochalcone, alitame, miraculin and monellin; sugar alcohols such as sorbitol, mannitol, glycerol, lactitol, maltitol, and xylitol; sugars extracted from sugar cane and sugar beet (sucrose), dextrose (also called glucose), fructose (also called laevulose), and lactose (also called milk sugar); isomalt, stevia, and mixtures thereof.

Examples of coloring agents include lakes and dyes approved as a food additive.

Examples of fillers that may be used include corn syrup, sucrose, starches, fats, proteins and gelatin. Additional materials that may be used in the soft chew base include corn syrup solids, sucrose, starches, fats, proteins and/or gelatin.

In one embodiment the dosage form is coated. The dosage form may be coated with a sugar or sugar alcohol-based coating or a film coating. Examples of materials for sugar or sugar alcohol-based coatings include but are not limited to sucrose, dextrose or xylitol. Examples of polymers for use in a film coating include but are not limited to hypromellose and polyvinyl alcohol and polyvinyl alcohol:polyethylene glycol co-polymers and mixtures thereof.

The amount of famotidine may be from about 2 to about 30 mg and the amount of the antacid(s) from about 200 to about 3000 mg. The amount of famotidine within the lipid bead portion may be from about 5 percent to about 40 percent, or from about 10 percent to about 30 percent by weight of the lipid bead portion.

The histamine H2-receptor antagonist such as famotidine may be present in an amount of from about 2 mg to about 30 mg, such as 4 mg to 20 mg or 8 mg to 12 mg or 2, 3, 4, 5, 6, 7, 8, 9, 10, 11, 12, 13, 14, 15, 16, 17, 18, 19, 20, 21, 22, 23, 24, 25, 26, 27, 28, 29 or 30 mg.

The antacid may be present in an amount of from about 200 to about 3000 mg. If two different antacids are utilized, they may be in the same amount or different amounts depending on the specific combinations. Examples are a dosage form having calcium carbonate in an amount from about 400 to about 1000 mg, such as 600, 700, 800, 900 or 1000 mg and magnesium hydroxide in an amount from about 50 to about 300 mg, such as about 100-about 200 mg, such as 100, 110, 120, 130, 140, 150, 160, 165, 170, 180, 190 or 200 mg. If aluminum oxide or aluminum hydroxide is used it may be used in an amount from about 200 to about 600 mg, such as 300, 400, 500 or 600 mg.

In another aspect the invention relates to a soft chewable tablet, wherein the encapsulated active pharmaceutical ingredient is loperamide and the other active pharmaceutical ingredient is at least one simethicone.

It is also desirable for the lipid bead containing famotidine and the surrounding soft chew base containing antacid to have a similar texture upon chewing. The texture can be determined through analysis of force over time. In this aspect of the invention, the force-over-time total area difference is less than 10000 g/sec between the lipid bead and the soft chew base.

In another aspect of the invention the famotidine does not degrade over time. In this aspect the amount of total famotidine impurities in the dosage form is less than 1.5% when stored at 40° C. and 75% relative humidity for 3 months, and less than 1.0% for any single impurity when stored at 40° C. and 75% relative humidity for 3 months.

The following examples are intended to illustrate, but not to limit, the invention in any manner, shape, or form, either explicitly or implicitly.

Example 1: Preparation of Famotidine Bead (Insert) in Meltable Edible Matrix

The famotidine hot melt solution and integrated soft chew were prepared as follows:

1. Approximately 30 g batches were prepared according to the base ratio formula in Table 1.
2. Materials in the meltable edible matrix were melted in a stainless-steel vessel at approximately 70° C. Famotidine was dispersed in the molten material and was continuously mixed to maintain uniform distribution.
3. A pipette was used to transport measured amount of molten mixture to form beads which then solidified upon cooling.
4. Variations in separate materials within the Base formula are shown in Table 2

TABLE 1

| Base Famotidine Bead Edible Matrix Formula | | |
|---|---|---|
| Ingredient | mg/Bead | % W/W |
| Meltable Edible Matrix* | 56.7 | 85.00 |
| Famotidine (Fine Powder) | 10.0 | 15.00 |
| TOTAL | 66.7 | 100.00 |

*Lipophilic thermoplastic material which in some examples also contains a plasticizer to soften the material.

TABLE 2

| Initial Ingredients for Famotidine Containing Beads | | |
|---|---|---|
| Ingredient | mg/Tab | % W/W |
| FORMULA 1 | | |
| SP Crodacol CS50[1] (Cetostearyl alcohol) | 56.67 | 85.00 |
| Famotidine | 10.00 | 15.00 |
| | 66.67 | 100.00 |
| FORMULA 2 | | |
| Compritol 888 ATO[2] (Glyceryl dibehenate) | 56.67 | 85.00 |
| Famotidine | 10.00 | 15.00 |
| | 66.67 | 100.00 |
| FORMULA 3 | | |
| Geleol[3] (mono/diglycerides, NF) | 56.67 | 85.00 |
| Famotidine | 10.00 | 15.00 |
| | 66.67 | 100.00 |
| FORMULA 4 | | |
| Sterotex (Hydrogenated cottonseed oil, NF) | 56.67 | 85.00 |
| Famotidine | 10.00 | 15.00 |
| | 66.67 | 100.00 |
| FORMULA 5 | | |
| SP Crodacol CS50[1](Cetostearyl alcohol) | 43.34 | 65.00 |
| Gelucire[4] 50/13 (Stearoyl polyoxyl-32 Glycerides) | 13.33 | 20.00 |
| Famotidine | 10.00 | 15.00 |
| | 66.67 | 100.00 |
| FORMULA 6 | | |
| Compritol 888 ATO (Glyceryl dibehenate) | 43.34 | 65.00 |
| Gelucire 50/13 (Stearoyl polyoxyl-32 Glycerides) | 13.33 | 20.00 |
| Famotidine | 10.00 | 15.00 |
| | 66.67 | 100.00 |

[1]Commercially available from the Croda Corporation
[2]Commercially available from the Gattefosse Corporation
[3]Commercially available from the Gattefosse Corporation
[4]Commercially available from the Gattefosse Corporation

Example 2: Stability Evaluation

The beads from Example 1 (Formulas 1-6) were exposed to different conditions in amber glass jars to determine the stability of Famotidine. The famotidine and famotidine impurity assay was analyzed versus a stock standard famotidine solution prepared at 400 μg/mL, using an HPLC with the following parameters:

Column: Advanced Chromatography Technologies (ACE) C8, 3 μm (150 mm×4.6 mm I.D.), ACE-112-1546

Mobile Phase: Gradient method of Sodium Phosphate Buffer:ACN (98:2v/v to 30:70 over 26 minutes)

Flow rate: 1.0 mL/min

Injection volume: 15 mL

UV Detector at 278 nm

Sample preparation included the following steps:

For samples containing glyceryldibehenate (Compritol): 50 mL chloroform was added and swirled until dissolved. Diluted to volume, with chloroform and mixed well.

For samples containing cetostearyl alcohol (Crodacol): 50 mL methanol was added and mixed using mechanical shaker until dissolved. Diluted to volume, with methanol and mixed well.

PART A: Storage in Amber Glass Jars:

Table 3 summarizes the stability study results.

TABLE 3

| Stability Study Results-Beads Stored in Amber Glass Jars | | | | | | | |
|---|---|---|---|---|---|---|---|
| Sample | Condition | Assay | FAM-A1[a] | FAM-A3[b] | FAM-A6[c] | FAM-UDP[d] | FAM-UDP2[d] |
| Formula 1 | 2 Weeks, RT | 104.3 | Not detected | 0.125 | Not detected | 0.145 | Not detected |
| Formula 2 | 2 Weeks, RT | 101.9 | Not detected | 0.124 | Not detected | 0.141 | Not detected |
| Formula 3 | 2 Weeks, RT | 104.3 | Not detected | 0.123 | Not detected | 0.149 | Not detected |
| Formula 4 | 2 Weeks, RT | 103.8 | Not detected | 0.119 | 0.144 | 0.136 | Not detected |
| Formula 5 | 2 Weeks, RT | | Not detected | | | | |
| Formula 6 | 2 Weeks, RT | | Not detected | | | | |
| Formula 1 | 2 Weeks, 40° C/75% RH | 103.2 | Not detected | 0.122 | Not detected | 0.140 | Not detected |
| Formula 2 | 2 Weeks, 40° C/75% RH | 100.6 | Not detected | 0.124 | Not detected | 0.158 | Not detected |
| Formula 3 | 2 Weeks, 40° C/75% RH | 102.6 | Not detected | 0.123 | 0.17 | 0.169 | Not detected |
| Formula 4 | 2 Weeks, 40° C/75% RH | 103.4 | Not detected | 0.123 | Not detected | 0.141 | Not detected |
| Formula 5 | 2 Weeks, 40° C/75% RH | | Not detected | | | | |
| Formula 6 | 2 Weeks, 40° C/75% RH | | Not detected | | | | |
| Formula 1 | 3 Months, RT | 130.3 | Not detected | 0.158 | 0.1 | 0.128 | Not detected |
| Formula 2 | 3 Months, RT | 121.2 | Not detected | 0.142 | 0.127 | 0.122 | Not detected |
| Formula 3 | 3 Months, RT | 120.3 | Not detected | 0.139 | 0.125 | 0.125 | Not detected |
| Formula 4 | 3 Months, RT | 123.4 | Not detected | 0.145 | 0.122 | 0.124 | Not detected |
| Formula 5 | 3 Months, RT | 100.0 | Not detected | 0.115 | | 0.096 | Not detected |
| Formula 6 | 3 Months, RT | 94.8 | 0.102 | 0.110 | 0.107 | 0.118 | Not detected |
| Formula 1 | 3 Months, 40° C/75% RH | 123.4 | Not detected | 0.151 | 0.095 | 0.121 | Not detected |
| Formula 2 | 3 Months, 40° C/75% RH | 126.5 | Not detected | 0.161 | 0.107 | 0.219 | Not detected |
| Formula 3 | 3 Months, 40° C/75% RH | 112.1 | Not detected | 0.152 | 0.107 | 0.605 | 0.731 |
| Formula 4 | 3 Months, 40° C/75% RH | 124.9 | Not detected | 0.156 | 0.131 | 0.125 | Not detected |
| Formula 5 | 3 Months, 40° C/75% RH | 94.8 | Not detected | 0.112 | Not detected | 0.091 | Not detected |
| Formula 6 | 3 Months, 40° C/75% RH | 99.0 | Not detected | 0.118 | Not detected | 0.277 | Not detected |

[a]FAM-A1: Famotidine Impurity A1
[b]FAM-A3: Famotidine Impurity A3
[c]FAM-A6: Famotidine Impurity A6
[d]FAM UDP: Famotidine Unspecified Degradation Product
RT - Room Temperature
RH - Relative Humidity Part B: Open Dish Storage The formulas in SAMPLES 1 and 2 were selected for Open Dish Stability evaluation. The samples were placed into an open dish and placed into the respective stability environment.

Table 4 summarizes the stability results of Famotidine in the beads during an Open Dish Study at 40° C./75% RH (relative humidity) for 3 months. Minimum degradation of Famotidine was observed after 3 months.

TABLE 4

| Stability Study Results-Open Dish Stability | | | | | | | |
|---|---|---|---|---|---|---|---|
| Sample | Condition | Assay | FAM-A1 | FAM-A3 | FAM-A6 | FAM-UDP | FAM-UDP2 |
| Formula 1 | Initial | 100.4 | Not detected | 0.119 | Not detected | 0.107 | Not detected |
| Formula 2 | Initial | 126.1 | Not detected | 0.148 | Not detected | 0.135 | Not detected |

TABLE 4-continued

| Stability Study Results-Open Dish Stability | | | | | | | |
|---|---|---|---|---|---|---|---|
| Sample | Condition | Assay | FAM-A1 | FAM-A3 | FAM-A6 | FAM-UDP | FAM-UDP2 |
| Formula 1 | 2 Weeks, 40° C./75% RH | 98.6 | Not detected | 0.117 | Not detected | 0.094 | Not detected |
| Formula 2 | 2 Weeks, 40° C./75% RH | 120.0 | Not detected | 0.146 | Not detected | 0.126 | Not detected |
| Formula 1 | 4 Weeks, 40° C./75% RH | 100.2 | Not detected | 0.133 | Not detected | 0.112 | Not detected |
| Formula 2 | 4 Weeks, 40° C./75% RH | 115.8 | Not detected | 0.151 | Not detected | 0.133 | Not detected |
| Formula 1 | 3 Months, 40° C./75% RH | 101.7 | Not detected | 0.157 | Not detected | Not detected | 0.12 |
| Formula 2 | 3 Months, 40° C./75% RH | 123.4 | 0.102 | 0.181 | Not detected | Not detected | 0.15 |

Example 3: Samples with Various Levels of Medium Chain Triglycerides (MCTs) & Force Measurement In order to soften the beads so that the texture is similar to the soft chew, different levels of MCT were added to Crodacol and Compritol as shown in Table 5, with associated force measurements.

Force Measurements were analyzed to compare the beads in Table 5 to the commercial Rolaids® Soft Chew, to more closely match the organoleptic texture between a soft chew ingredient and the bead. Hardness was measured using a Texture Profile Analyzer with the following test parameters:

Material Thickness—Solid block approx. 20 mm

Probe—Replaceable needle probe

Load cell—5 Kg

Test Profile—2 mm penetration @ 0.2 mm/sec

Results: Blends containing 30% MCT oil had the lowest hardness values (not included in graph). For stability studies, 15% MCT oil was selected to minimize leaching of the oil from the bead into the soft chew matrix.

TABLE 5

| Samples with Various levels of MCTs | | |
|---|---|---|
| All contain 15% Famotidine | Formula | Force measurement Area F-T 1:2 (g · sec) |
| Crodacol without MCT | Formula 7 | 24,217.775 |
| Compritol without MCT | Formula 8 | 16,318.691 |
| Crodacol 15% MCT | Formula 9 | 13,159.655 |
| Compritol 15% MCT | Formula 10 | 8,805.754 |
| Crodacol 20% MCT | Formula 11 | 9,599.951 |
| Compritol 20% MCT | Formula 12 | 7,040.707 |
| Crodacol 30% MCT | Formula 13 | 8713.572 |
| Compritol 30% MCT | Formula 14 | 4254.296 |
| Soft Chew | | |
| **Rolaids ® Chew Commercial 2** | 6312A | 858.712 |

FIG. 1 shows the force measurements on samples with different amounts of MCTs,

Example 4: Stability of Famotidine Beads in a Soft Chew

The Rolaids® softchew was used for a base stability study when combined with the famotidine beads. The stability results are shown in Table 7.

The bead ingredients for use in combination with the Softchew are shown in Table 6.

TABLE 6

| Ingredients combined with Softchew | | |
|---|---|---|
| Ingredient | mg/Tab | % W/W |
| FORMULA 15 | | |
| Compritol 888 ATO (Glyceryl dibehenate) | 46.7 | 70.00 |
| Labrafac Lipophile WL 1349 (MCT oil)* | 10.0 | 15.00 |
| Famotidine | 10.0 | 15.00 |
| | 66.7 | 100.00 |
| FORMULA 16 | | |
| SP Crodacol CS50 (Cetostearyl alcohol) | 46.7 | 70.00 |
| Labrafac Lipophile WL 1349 (MCT oil)* | 10.0 | 15.00 |
| Famotidine | 10.0 | 15.00 |
| | 66.7 | 100.00 |

*MCT Oil was added to soften the bead matrix

Sample Prep for Stability Study: 5 gm Rolaids® Softchew was cut into 6 pieces. Approximately total of 200 mg of beads with Famotidine were weighed out for each test condition. One or two beads were inserted into each cut chew piece, and was performed twice for each condition.

Sample Storage: Samples were placed in an amber jar and placed on stability at initial and 40 C/75% RH for 2 weeks, 4 weeks, 2 months and 3 months timepoints.

The following ingredients are displayed on the package for the commercial Rolaids® Softchew.

Active Ingredients

In Each Chew: Calcium Carbonate USP (1330 mg), Magnesium Hydroxide USP (235 mg).

Inactive Ingredients

Corn Starch, Corn Syrup, Corn Syrup Solids, Glycerin, Hydrogenated Coconut Oil, Lecithin, Natural and Artificial Flavors, Red 40 Lake, Sucrose, Water.

Other Information

Each chew contains: calcium 535 mg, magnesium 100 mg. Store between 68 degrees to 77 degrees F. (20 degrees to 25 degrees C.) in a dry place.

TABLE 7

Stability Results for Famotidine Bead combined with Soft Chew

| Sample | Condition | Assay | FAM-A1[a] | FAM-A3[b] | FAM-A6[c] | FAM-UDP | FAM-UDP2 |
|---|---|---|---|---|---|---|---|
| Formula 15 + Soft Chew | | | | | | | |
| Sample 1 | Initial | 122.0 | 0.062 | 0.148 | Not detected | 0.161 | Not detected |
| Sample 2 | Initial | 122.1 | 0.063 | 0.148 | Not detected | 0.157 | Not detected |
| Sample 3 | 2 Weeks, 40° C./75% RH | 121.6 | 0.095 | 0.154 | Not detected | Not detected | 0.150 |
| Sample 4 | 2 Weeks, 40° C/75% RH | 125.8 | 0.101 | 0.160 | 0.045 | Not detected | 0.156 |
| Sample 5 | 4 Weeks, 40° C/75% RH | 123.5 | 0.097 | 0.160 | Not detected | Not detected | 0.145 |
| Sample 6 | 4 Weeks, 40° C/75% RH | 121.0 | 0.094 | 0.155 | Not detected | Not detected | 0.149 |
| Sample 7 | 2 Months, 40° C/75% RH | 114.8 | 0.086 | 0.143 | 0.054 | Not detected | 0.128 |
| Sample 8 | 2 Months, 40° C/75% RH | 116.2 | 0.086 | 0.144 | 0.053 | Not detected | 0.131 |
| Sample 9 | 2 Months, 40° C/75% RH | 98.4 | 0.073 | 0.122 | 0.062 | Not detected | 0.111 |
| Sample 10 | 2 Months, 40° C/75% RH | 94.3 | 0.067 | 0.115 | 0.052 | Not detected | 0.107 |
| Sample 11 | 3 Months, 40° C/75% RH | 123.0 | 0.065 | 0.146 | Not detected | Not detected | 0.118 |
| Sample 12 | 3 Months, 40° C/75% RH | 121.5 | 0.074 | 0.144 | 0.039 | Not detected | 0.119 |
| Sample 13 | 3 Months, 40° C/75% RH | 98.0 | Not detected | 0.111 | Not detected | Not detected | 0.088 |
| Sample 14 | 3 Months, 40° C/75% RH | 97.1 | 0.044 | 0.108 | 0.043 | Not detected | 0.091 |
| Formula 16 + Soft Chew | | | | | | | |
| Sample 1 | Initial | 99.1 | 0.048 | 0.121 | Not detected | 0.129 | Not detected |
| Sample 2 | Initial | 99.8 | 0.05 | 0.122 | Not detected | 0.129 | Not detected |
| Sample 3 | 2 Weeks, 40° C/75% RH | 88.4 | 0.044 | 0.110 | Not detected | Not detected | 0.188 |
| Sample 4 | 2 Weeks, 40° C/75% RH | 95.9 | 0.074 | 0.122 | 0.060 | Not detected | 0.393 |
| Sample 5 | 4 Weeks, 40° C/75% RH | 86.3 | 0.064 | 0.112 | Not detected | Not detected | 0.280 |
| Sample 6 | 4 Weeks, 40° C/75% RH | 92.6 | 0.070 | 0.120 | 0.054 | Not detected | 0.317 |
| Sample 7 | 2 Months, 40° C/75% RH | 74.7 | Not detected | 0.091 | Not detected | Not detected | 0.095 |
| Sample 8 | 2 Months, 40° C/75% RH | 72.0 | Not detected | 0.087 | Not detected | Not detected | 0.091 |
| Sample 9 | 3 Months, 40° C/75% RH | 63.0 | Not detected | 0.072 | Not detected | Not detected | 0.057 |
| Sample 10 | 3 Months, 40° C/75% RH | 63.5 | Not detected | 0.073 | Not detected | Not detected | 0.059 |

Example 5: Coated Particulates and Dosage Form

Part A: Famotidine Granulation

TABLE 8

Granulation ingredients for Famotidine Particles (1.5 kg batch)

| | % (w/w) | Grams for 1.5 kg batch |
|---|---|---|
| Lactose Monohydrate, Impalpable NF | 81.00 | 1215 |
| Famotidine USP | 13.00 | 195 |
| Hypromellulose E5 Premium USP | 6.00 | 90 |
| Purified Water USP | xxx | 810 |

1. Lactose Monohydrate & Famotidine were passed through a 40 mesh screen.
2. Two-thirds of total water was heated to 70-80° C. The Hypromellose was slowly added to water while mixing using a high shear mixer. The remaining water was added. The solution was cooled and allowed to de-aerate.
3. Granulation was carried out in a Huttlin Diskj et unit by spraying the granulating fluid from Step 2 at 50 cc/min. After granulation was completed, the particles were dried and discharged for hot melt coating.
4. After granulation, pass material through 18 mesh before hot melt coating.

Part B: Hot Melt Coating

For hot melt coating, Glyceryl palmitostearate (commercially available as Precirol ATO from the Gattefosse corporation) is heated to a temperature of about 60° C.

and sprayed on Famotidine granulation from Part A, in the Huttlin Diskj et unit. The particles were coated with 30% weight gain.

Part C: Soft Chew Formulation Incorporating Coated Particulates

The following dosage form was prepared using the famotidine coated particles in Part A.

TABLE 9

| | With Famotidine (g/batch) | % | mg/5 g piece |
|---|---|---|---|
| Dextrose Equivalent 42 Corn Syrup-Cooked (85% solids) | 126 | 31.5 | 1575 |
| Calcium Carbonate | 64 | 16 | 800 |
| Mag Hydroxide | 13.2 | 3.3 | 165 |
| Coated Famotidine | 12.4 | 3.1 | 155 |
| Confectionary 10X Sugar | 116 | 29 | 1450 |
| Corn Syrup Solids | 32 | 8 | 400 |
| Sucralose | 2.8 | 0.7 | 35 |
| Glycerin | 6 | 1.5 | 75 |
| Coconut Oil | 24 | 6 | 300 |
| Lecithin | 2.4 | 0.6 | 30 |
| Flavors | 1.2 | 0.3 | 15 |
| Total | 400 | 100 | 5000 |

Note:
Coated Famotidine is at 6.5% potency

1. Blending process: The 42 Corn syrup was heated to 90° C. and blended with the glycerin using a laboratory overhead mixer.
2. The Confectionery sugar, calcium carbonate, magnesium hydroxide, corn syrup solids were added to the liquid blend in Step 1.
3. In a separate container Coconut oil was heated to 40-45° C. and blended with Lecithin.
4. The coated famotidine particles from Part A were blended with Coconut oil and Lecithin mixture and then added to the blend from Step 2. The flavor and color were added at the end. The temperature of the final mixture was approximately 40° C. during the addition of coated famotidine.
5. The soft chew blend was mixed until uniform.
6. The blend was cooled and solidified and manually cut into 5 g pieces.

The invention claimed is:

1. A method for treating a subject suffering from a disease or disorder in the gastro intestinal tract comprising administering a soft chewable dosage form comprising a first active pharmaceutical ingredient encapsulated in a lipid material/matrix comprising a first lipid and a second lipid, wherein the second lipid is a plasticizer, wherein the lipid encapsulated active pharmaceutical ingredient is embedded in the soft chewable dosage form, and wherein the soft chewable dosage form comprises at least a second active pharmaceutical ingredient.

2. A method according to claim 1, wherein the disease or disorder in the gastro intestinal tract is peptic ulcers, gastric ulcers, hyperacidity, gastroesophageal reflux disease (GERD), or gastritis.

3. A method according to claim 1, wherein the disease or disorder in the gastro intestinal tract leads to heartburn, gas, indigestion, upper abdominal fullness, heartburn, nausea, belching, upper abdominal pain, or feeling full earlier than expected when eating.

* * * * *